(12) United States Patent
Hennemeyer et al.

(10) Patent No.: US 11,931,239 B2
(45) Date of Patent: Mar. 19, 2024

(54) PERCUTANEOUS VASCULAR ANASTOMOSIS

(71) Applicant: ARIZONA BOARD OF REGENTS ON BEHALF OF THE UNIVERSITY OF ARIZONA, Tucson, AZ (US)

(72) Inventors: Charles T. Hennemeyer, Tucson, AZ (US); Adam Gold, Scottsdale, AZ (US)

(73) Assignee: ARIZONA BOARD OF REGENTS ON BEHALF OF THE UNIVERSITY OF ARIZONA, Tucson, AZ (US)

( * ) Notice: Subject to any disclaimer, the term of this patent is extended or adjusted under 35 U.S.C. 154(b) by 306 days.

(21) Appl. No.: 16/973,571

(22) PCT Filed: Aug. 1, 2019

(86) PCT No.: PCT/US2019/044716
§ 371 (c)(1),
(2) Date: Dec. 9, 2020

(87) PCT Pub. No.: WO2020/028695
PCT Pub. Date: Feb. 6, 2020

(65) Prior Publication Data
US 2021/0244524 A1    Aug. 12, 2021

Related U.S. Application Data

(60) Provisional application No. 62/713,303, filed on Aug. 1, 2018.

(51) Int. Cl.
*A61F 2/06* (2013.01)

(52) U.S. Cl.
CPC ........ *A61F 2/064* (2013.01); *A61F 2002/061* (2013.01)

(58) Field of Classification Search
CPC ................ A61F 2/064; A61F 2002/061; A61F 2002/065; A61F 2/07; A61F 2002/072; A61F 2002/075; A61B 2017/1135
See application file for complete search history.

(56) References Cited

U.S. PATENT DOCUMENTS

| | | | | |
|---|---|---|---|---|
| 5,540,712 A * | 7/1996 | Kleshinski | ................ | A61F 2/90 606/198 |
| 5,755,778 A * | 5/1998 | Kleshinski | .............. | A61F 2/856 623/1.13 |
| 2002/0019665 A1* | 2/2002 | Dehdashtian | ............. | A61F 2/07 623/1.13 |
| 2002/0033180 A1* | 3/2002 | Solem | ........................ | A61F 2/06 604/8 |
| 2004/0215220 A1* | 10/2004 | Dolan | .................... | A61B 17/11 623/1.11 |

(Continued)

*Primary Examiner* — Jing Rui Ou
(74) *Attorney, Agent, or Firm* — NGUYEN TARBET LLC

(57) ABSTRACT

Collapsible branched anastomosis devices allow for the formation of percutaneous vascular anastomoses using a Seldinger wire technique. This minimally invasive approach eliminates the need for a large surgical incision and also avoids the use of time consuming hand-suturing. The devices collapse to a fraction of their expanded volume and are configured to fit within a delivery sheath for over the wire delivery through a small incision in a blood vessel.

10 Claims, 13 Drawing Sheets

(56) References Cited

U.S. PATENT DOCUMENTS

| | | | |
|---|---|---|---|
| 2006/0095118 A1* | 5/2006 | Hartley | A61F 2/07 623/1.35 |
| 2008/0086193 A1* | 4/2008 | Thramann | A61F 2/07 623/1.13 |
| 2008/0195125 A1* | 8/2008 | Hoffman | A61B 17/11 606/153 |
| 2008/0319530 A1* | 12/2008 | Leewood | A61F 2/07 623/1.16 |
| 2010/0130995 A1* | 5/2010 | Yevzlin | A61B 17/11 606/153 |
| 2017/0165089 A1* | 6/2017 | Li | A61F 2/04 |

* cited by examiner

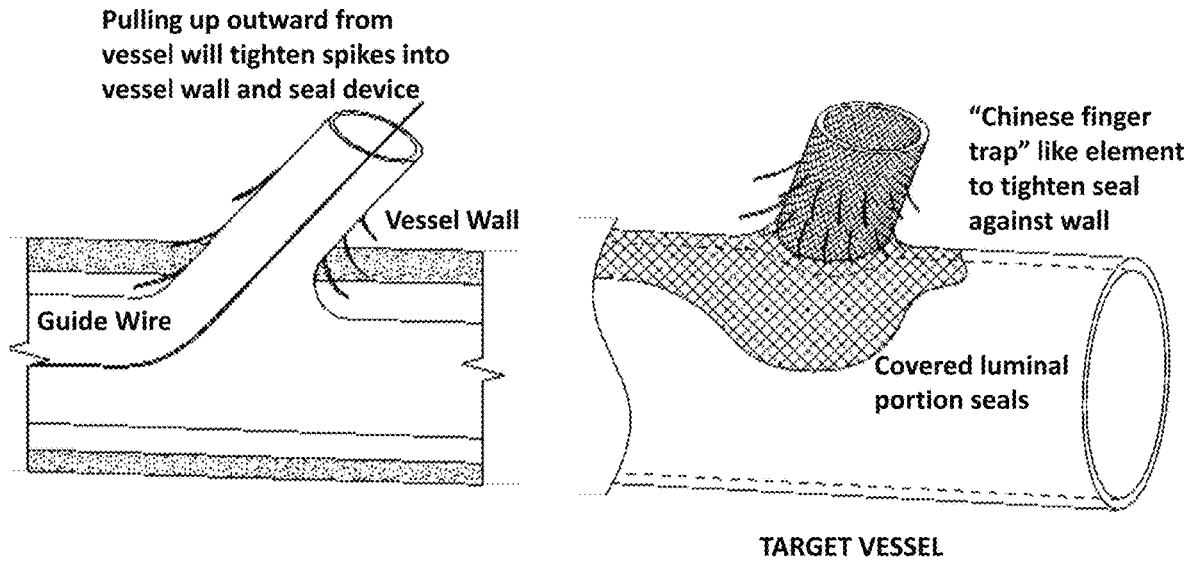
FIG. 9A
FIG. 9B
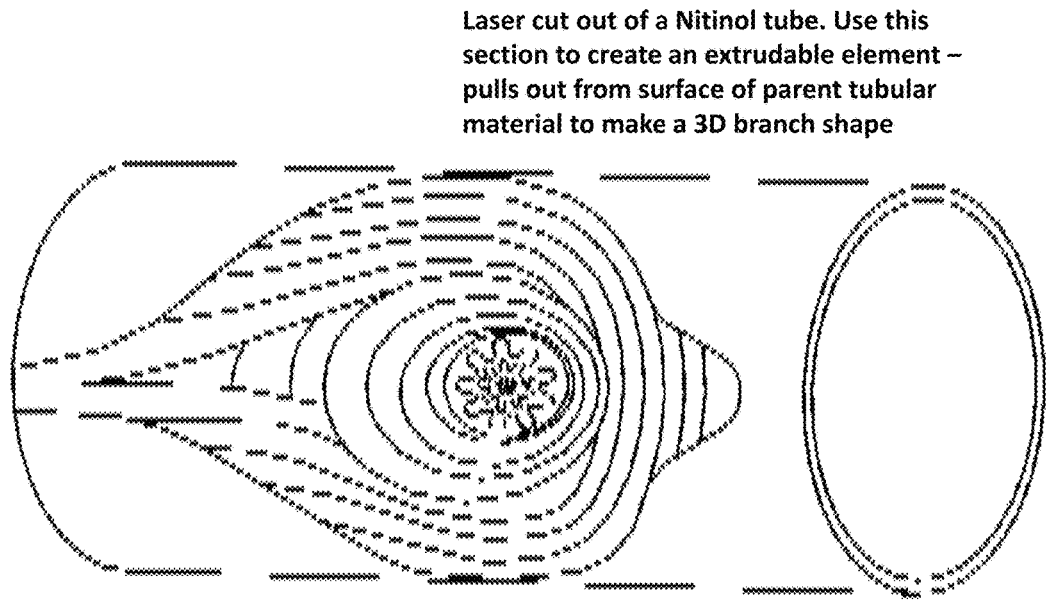
FIG. 10

Side View

Side View

Top View

Top View

PERCUTANEOUS VASCULAR ANASTOMOSIS

CROSS-REFERENCES TO RELATED APPLICATIONS

This application is a PCT application and claims benefit of U.S. Provisional Patent Application No. 62/713,303, filed Aug. 1, 2018, the specification of which is incorporated herein in its entirety by reference.

FIELD OF THE INVENTION

The present invention relates to devices and methods for forming percutaneous vascular anastomoses.

BACKGROUND OF THE INVENTION

Anastomosis is a surgical connection made between two hollow vessels such as blood vessels. In some cases, this connection forms a branched or y-shaped intersection between a main vessel and a branch vessel. One example of such an anastomosis is the formation of an arteriovenous graft for hemodialysis. In this example, two separate branches are formed, one from a vein and another from an artery, and the branches are connected with a tubular vessel.

The traditional surgical procedure involves hand-suturing the two vessels together such that the end of one vessel is fixedly attached to an opening of the second vessel. This approach is time consuming and requires a surgical incision to provide access to the vessel. Because the sutures must go all of the way around the new connection, so as to securely attach the two vessels, the incision must be large enough to allow considerable access for the surgeon.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

SUMMARY OF THE INVENTION

The present invention features devices and methods for forming percutaneous vascular anastomoses using a Seldinger wire technique. This Seldinger wire technique is a minimally invasive technique which provides access to blood vessels and other hollow organs. For example, using a Seldinger wire technique, a wire may be inserted into a vessel through a needle and a tube or catheter may be inserted into the vessel over the wire.

One of the unique and inventive technical features of the present invention is a collapsible branched anastomosis device with structural elements configured to expand and hold a desired shape for anastomosis. Without wishing to limit the invention to any theory or mechanism, it is believed that the technical feature of the present invention advantageously provides for minimally invasive formation of a percutaneous vascular anastomosis using a Seldinger wire technique. None of the presently known prior references or work has the unique inventive technical feature of the present invention.

It is surprising that the present invention allows for minimally invasive anastomosis using a Seldinger wire technique because an anastomosis is a complex branched connection of vessels. The traditional Seldinger technique does not allow for implantation of devices with multiple axes. While simple navigation of single-axis implants within a single-axis vessel is straightforward using a Seldinger wire technique, the present invention features a device designed for implantation using a Seldinger wire technique which has two separate axes. Such a two-axis device is potentially applicable to vascular and tubular anatomic problems in medicine. These multiple axis complicate the proper placement and expansion of the collapsed device. With a simple device like a collapsible blood vessel stent, proper placement is accomplished by positioning along a single axis and expansion about that axis. In contrast, the device of the present invention must have two separate branches properly placed about two separate axes and each branch properly expanded about its own respective axis. As the degree of device manipulation is limited using a Seldinger wire technique, it is surprising that the device of the present invention may be successfully implanted to form an anastomosis.

Additionally, the unique structure of the device of the present invention allows for a set angle between the two axes of the device, so as to hold the multiple branches open in a desired configuration. The degree to which the device holds itself open is called the radial force and is adjustable by typical engineering principals in stent design such as the angles of the collapsible structural elements make with each other, the relative thickness or amount of shape memory material dedicated to the areas that fold upon themselves. Very large outward radial forces may be generated simply with these commonly used methods. however all universally add to the final collapsed diameter which is undesirable. The ring design of the present invention minimizes the amount of structural material required to balance the needed outward radial force generation.

Furthermore, it is surprising that a complex branched anastomosis device having two axes, may be designed to collapse down about a single axis, and then expand in the body to retain a desired branched structure. For such a collapse to be possible without damaging the device, the device must be extremely flexible. However, in order to hold the newly formed anastomosis open for use, the device must have some amount of strength and rigidity. Surprisingly, the device of the present invention is not only able to collapse without damage and expand to hold the anastomosis open, but also to hold the two branches of the anastomosis at a desired angle.

The prior art teaches away from the present invention in that it teaches that the Seldinger wire technique may only be used to position devices within a vessel on one side of the incision into the vessel. Because the guidewire enters the vessel through the incision and continues down the vessel in only one direction, it has been commonly taught that the Seldinger wire technique allows for positioning of devices within the vessel only in the same direction of the guidewire. However, the device of the present invention is configured to have a portion of the device implanted within the vessel in the direction of the guidewire and another portion of the device implanted in a retrograde fashion within the target vessel, basically in the opposite direction of the wire as it enters the lumen of the target vessel. Further, the branching component of the device extends outside the lumen of the target vessel, crossing the wall and into the subcutaneous deeper tissues as it follows the guide wire towards the skin surface.

BRIEF DESCRIPTION OF THE DRAWINGS

The features and advantages of the present invention will become apparent from a consideration of the following detailed description presented in connection with the accompanying drawings in which:

FIG. 9A shows a schematic drawing of a device of the present invention having spikes at the base of the branch channel to tighten the device against the vessel wall.

FIG. 9B shows another schematic drawing of a device of the present invention having spikes at the base of the branch channel to tighten the device against the vessel wall.

FIG. 10 shows a schematic drawing of a device of the present invention having been cut out of a Nitinol tube to create an expandable element which can be pulled from the surface of the parent tubular material to make a three-dimensional branch shape.

DESCRIPTION OF PREFERRED EMBODIMENTS

As used herein, the term "anastomosis" refers to a connection between two vessels such as blood vessels. Structures other than blood vessels may also be connected by an anastomosis. The structures and vessels may be natural or synthetic. Some non-limiting examples include: vascular anastomosis, arterial anastomosis, colonic anastomosis, intestinal anastomosis, and anastomosis of veins, bile ducts, the large or small bowel, lymphatic vessels, the thoracic duct, or enteric viscera.

As used herein, the term "kirigami" refers to a pattern which is cut such that it forms a desired shape when it is pulled or folded.

Figure 1:
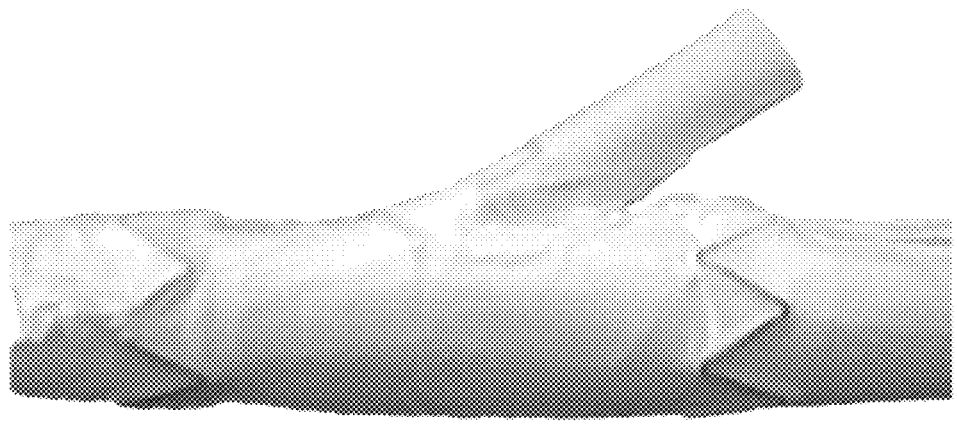
FIG. 1 shows a photograph of a collapsible branched anastomosis device of the present invention. The three collapsible rings can be seen through the poly-tetrafluoroethylene (PTFE) coating.
Figure 2:
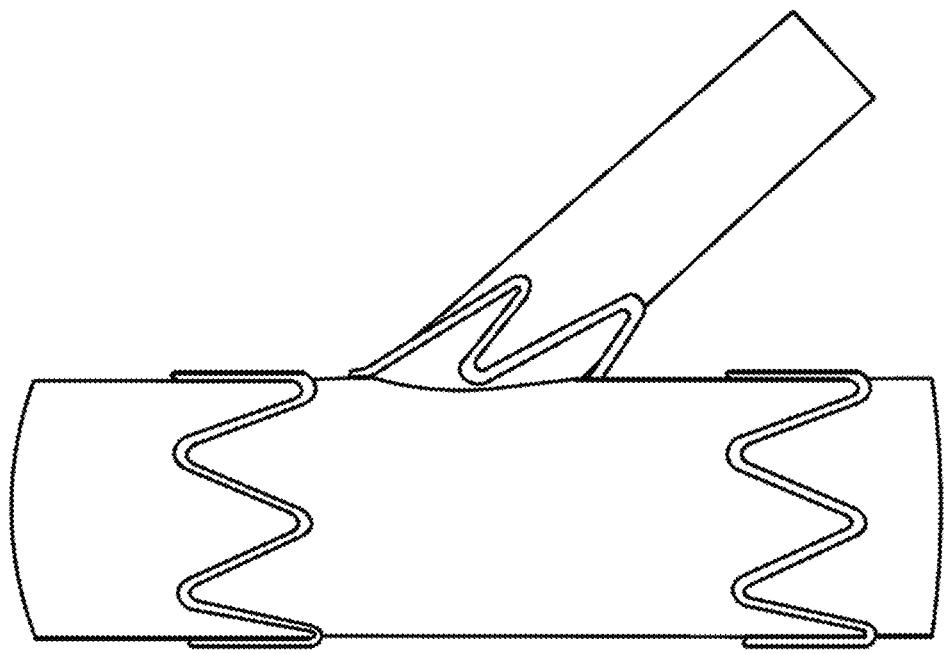
FIG. 2 shows a photograph of the three collapsible rings of a collapsible branched anastomosis device of the present invention in place on a manufacturing jig. This jig holds the rings in proper arrangement so that a PTFE coating can be applied to form the walls of the channels.

Referring now to FIG. 1, the present invention refers to a branched anastomosis device. As shown, the branch channel may have a smaller diameter than the main channel. Referring now to FIG. 2, the present invention may feature collapsible rings to hold the channels in an expanded position. Without wishing to limit the invention so any particular theory or mechanism, it is believed that these rings may be effective to form a seal between the device and a vessel. For example, these rings may press the walls of the device firmly against the walls of the vessel so as to prevent leakage between the device and the vessel.

Figure 3:
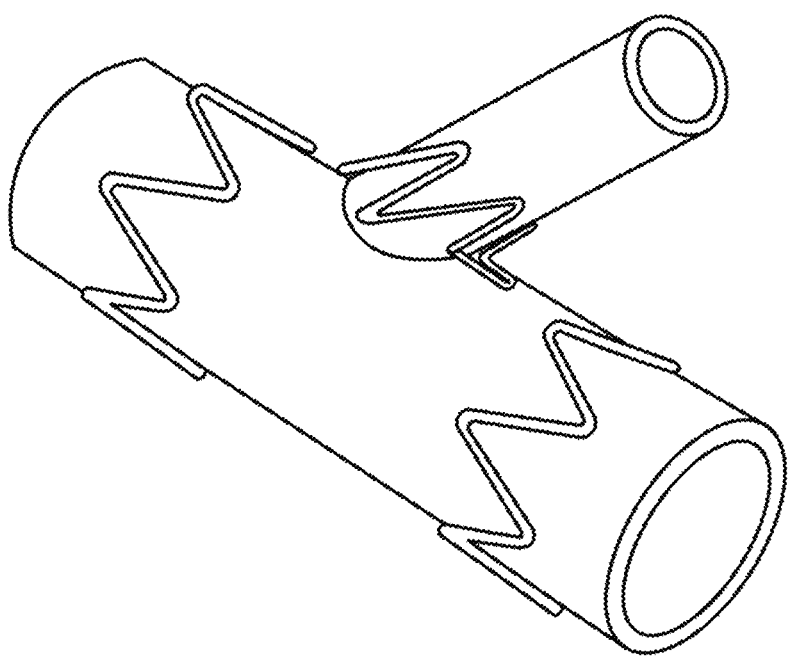
FIG. 3 shows another photograph of the three collapsible rings on the manufacturing jig. The barb of the branch channel proximal collapsible ring can be seen to match the angle of the jig.
Figure 4:
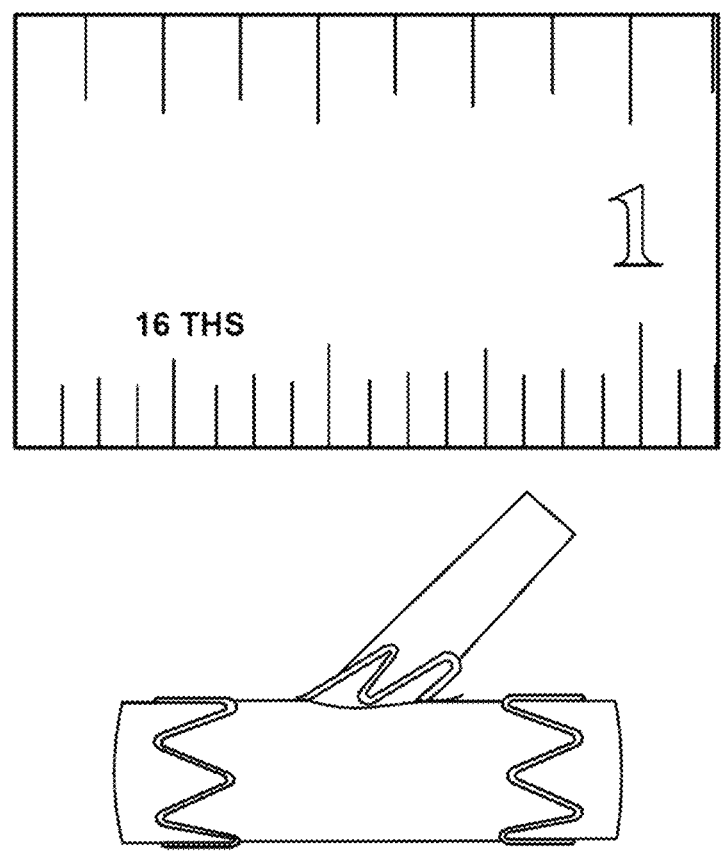
FIG. 4 shows a photograph of the manufacturing jig next to a ruler showing 1 inch for scale reference.

Referring now to FIG. 3, the present invention may feature devices which are smaller than a finger. These devices may be configured for use in major or minor vessels. Referring now to FIG. 4, the present invention may feature devices which are shorter than an inch.

Figure 5:
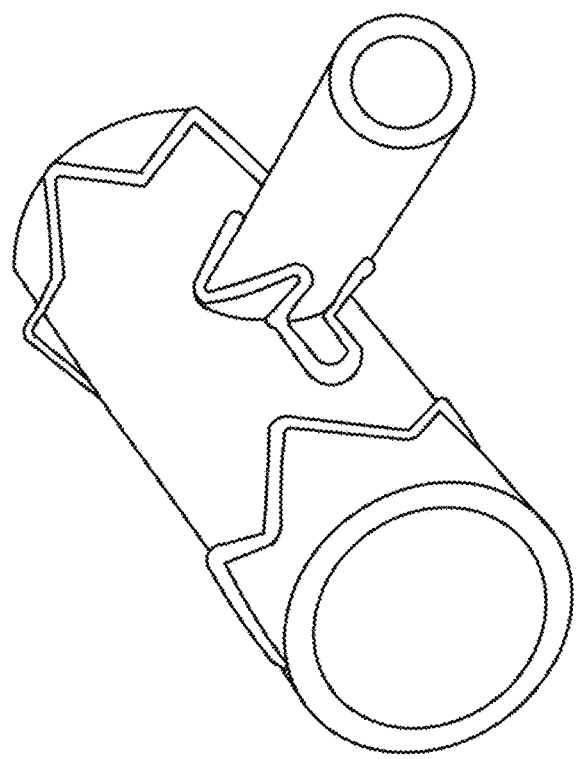
FIG. 5 shows another photograph of the three collapsible rings on the manufacturing jig. The barb of the branch channel proximal collapsible ring can be seen to match the angle of the jig.
Figure 6:
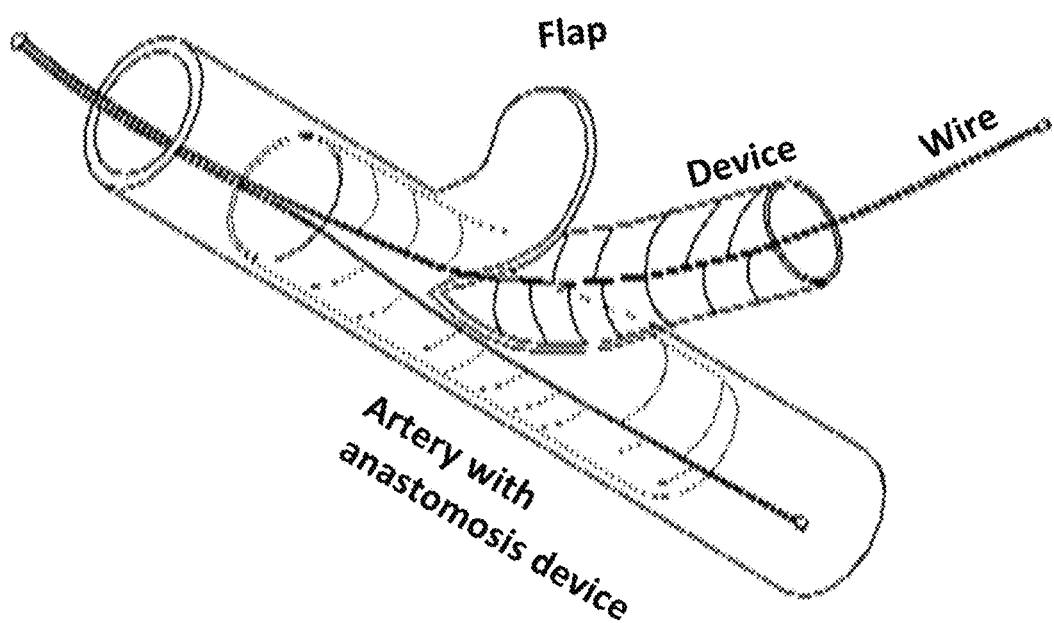
FIG. 6 shows a schematic drawing of the collapsible branched anastomosis device of the present invention inserted over a wire into an artery.

Referring now to FIG. 5, the present invention may feature devices which have wide channels. These channels may allow for unhindered flow of blood or other bodily fluids. Referring now to FIG. 6, the present invention may feature devices which can be inserted over a wire into an artery after a flap is cut in the artery.

Figure 7A:
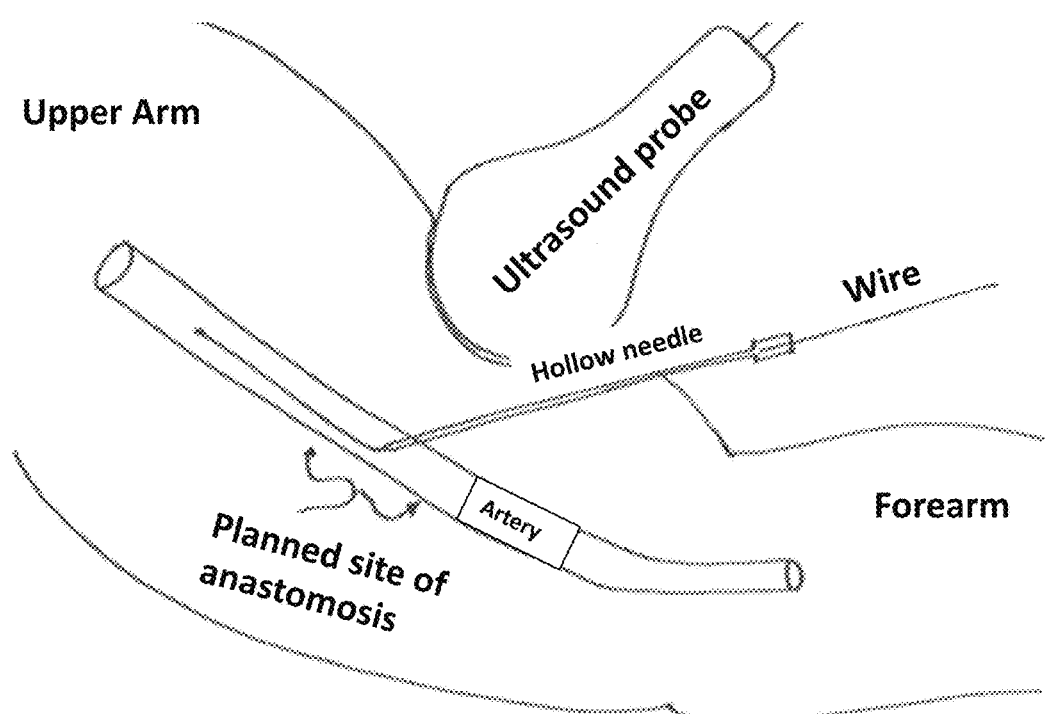
FIG. 7A shows a schematic drawing of a method of placing a device of the present invention into an artery using a Seldinger technique. An ultrasound probe is used to puncture an artery with a hollow needle at a planned site of anastomosis. A wire is then fed through the needle and into the artery.
Figure 7B:
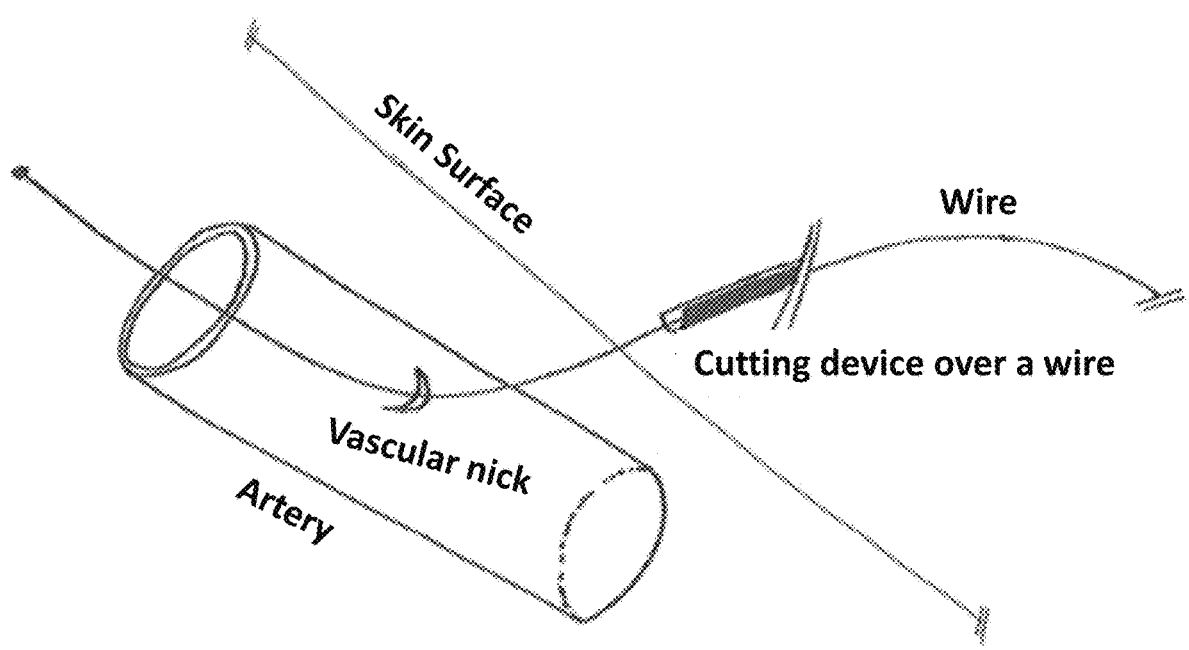
FIG. 7B shows a schematic drawing of a method of placing a device of the present invention into an artery using a Seldinger technique. A cutting device is passed over a wire to make an incision at a vascular nick to allow for the placement of the device within the artery.

Referring now to FIG. 7A, the present invention may use an ultrasound probe or other imaging device to guide a needle into an artery at a planned site of anastomosis. A wire may then be passed through the needle into the artery to allow for access of the artery by a Seldinger technique. Referring now to FIG. 7B, the present invention may feature a cutting device which is passed over the wire to make an incision in an artery which has a vascular nick. For example, the incision may be made at the desired site for the anastomosis.

Figure 8A:
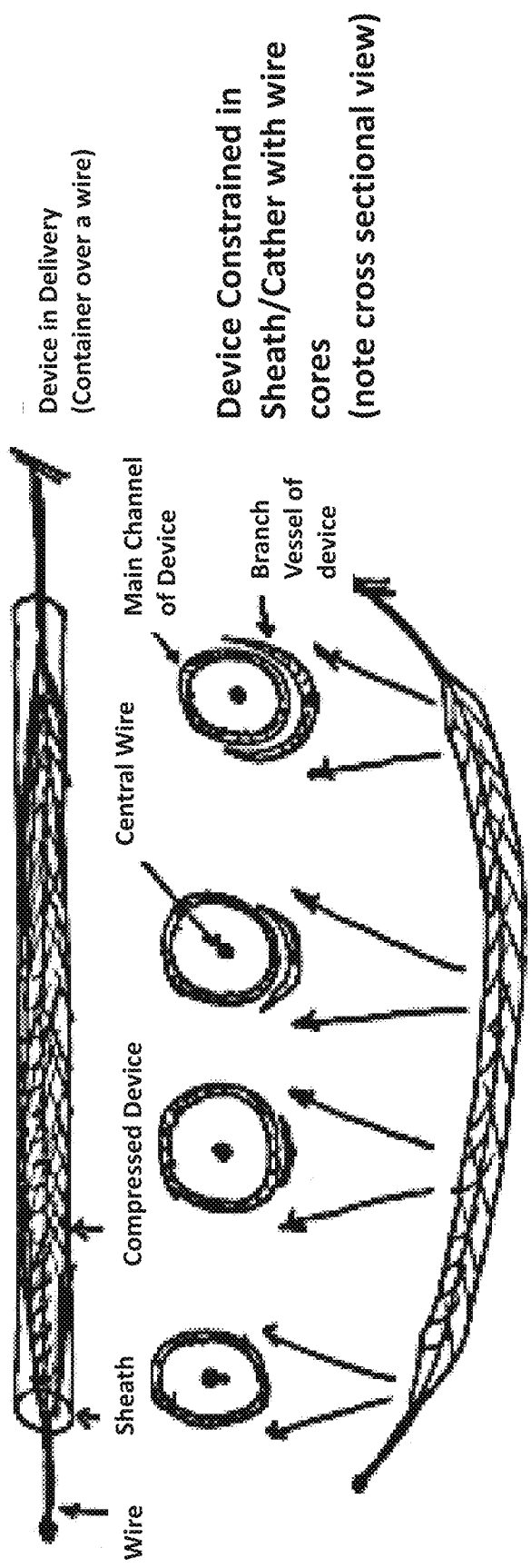
FIG. 8A shows a schematic drawing of a device of the present invention compressed for delivery and passed over a wire.
Figure 8B:
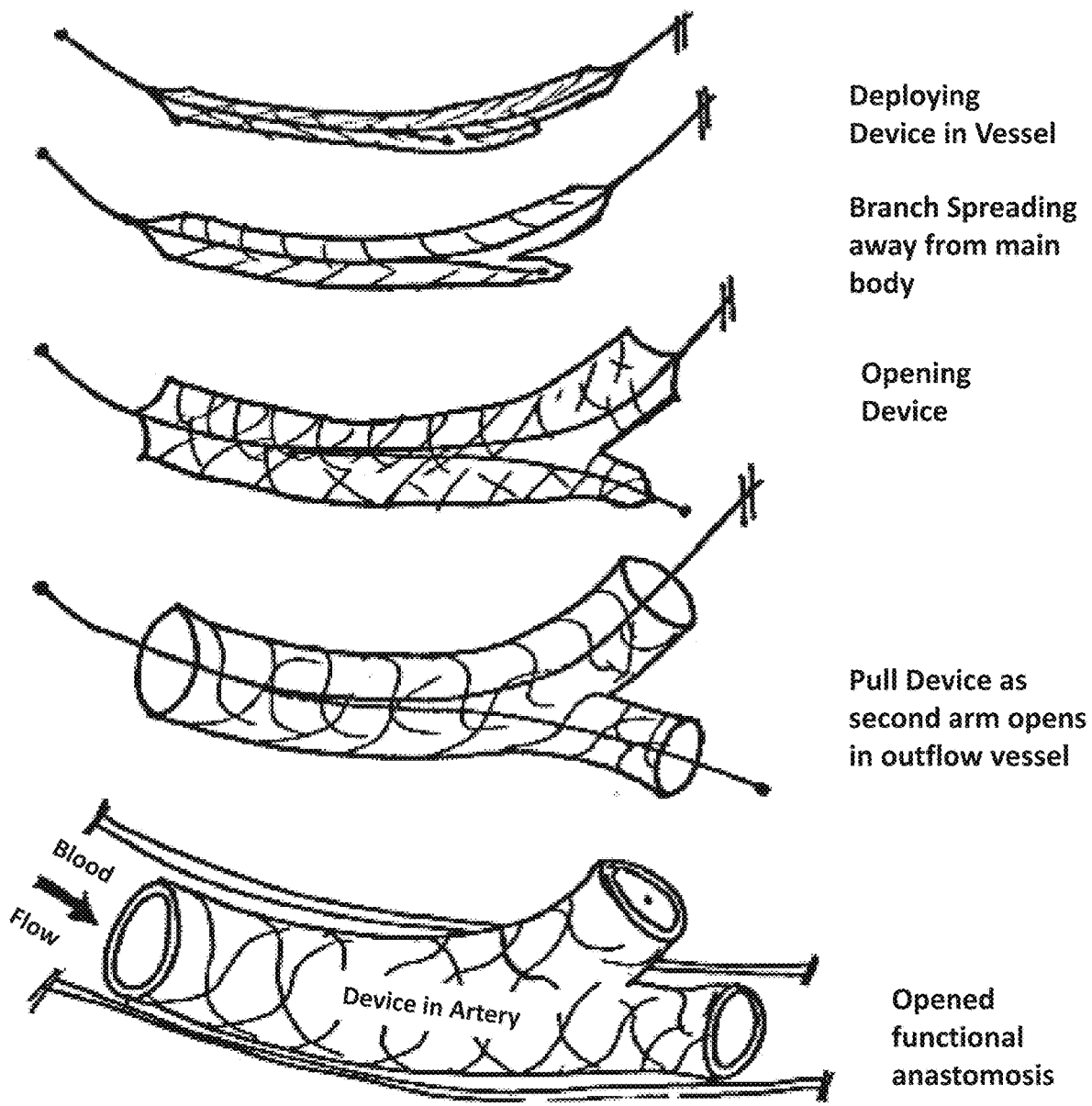
FIG. 8B shows a progression of schematic drawings illustrating the progression of expansion of a device of the present invention to form an opened functional anastomosis within an artery.

Referring now to FIG. 8A, the present invention may feature devices which can be collapsed within a delivery sheath such that both branches collapse about a single axis. Referring now to FIG. 8B, the present invention may feature methods for deploying the device in a vessel, spreading the branch away from the main body, opening the device, and pulling the device as the second arm opens in an outflow vessel to provide an opened functional anastomosis in an artery.

Referring now to FIG. 9A, the present invention may feature devices with spikes which tighten into a vessel wall to seal the device. Referring now to FIG. 9B, the present invention may feature devices which have a covered luminal portion which seals after a "Chinese finger trap" like element tightens a seal against the vessel wall. Referring now to FIG. 10, the present invention may feature devices which are Laser cut out of a nitinol tube. The cut section may create an extrudable element which may be pulled out from the surface of a parent tubular material to form a three dimensional branch shape.

Figure 11A:
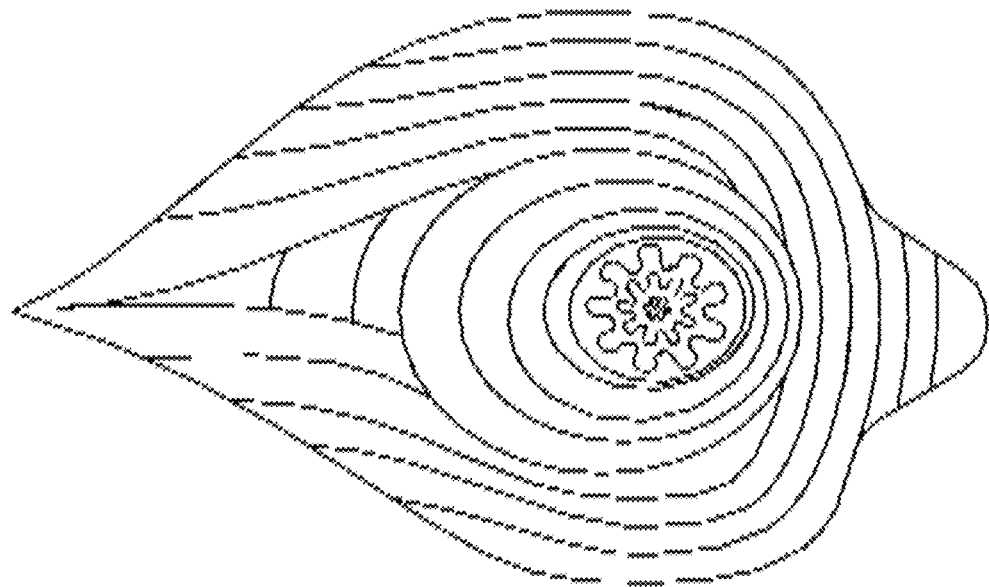
FIG. 11A shows a schematic drawing of a pattern to create an expandable element which can be pulled from the surface of the parent tubular material to make a three-dimensional branch shape.
Figure 11B:
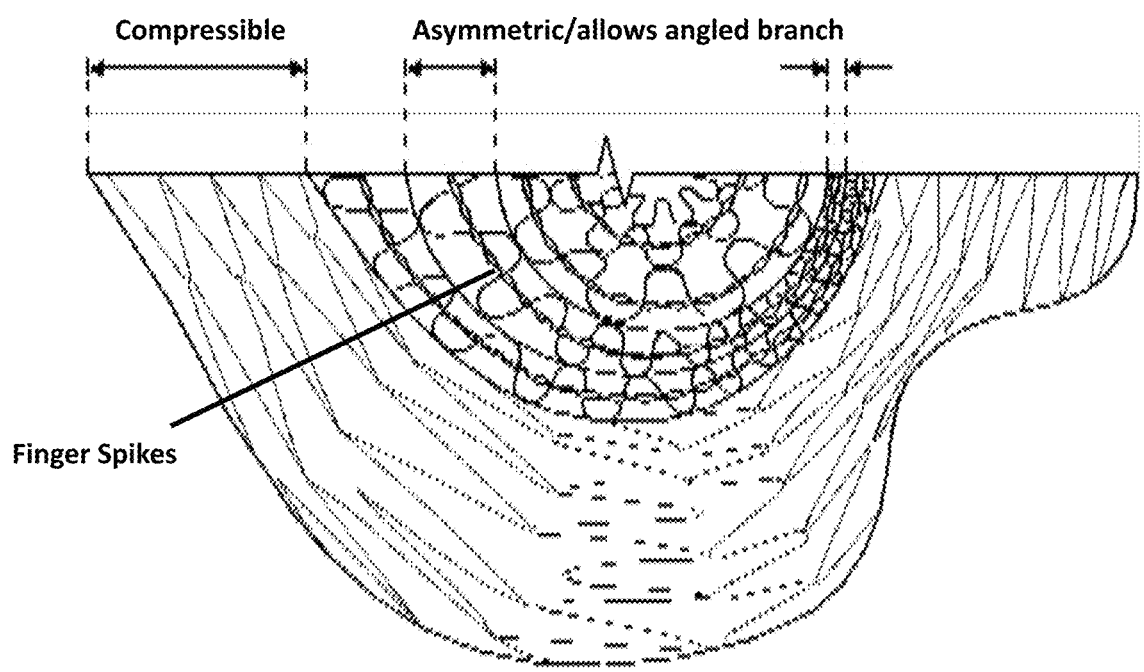
FIG. 11B shows another schematic drawing of a pattern to create an expandable element which can be pulled from the surface of the parent tubular material to make a three-dimensional branch shape.

Referring now to FIG. 11A, the present invention may feature devices which are cut from a single sheet of material. These devices may feature a flange to seal the branch channel against a vessel wall and optionally may not feature a main channel. Referring now to FIG. 11B, the present invention may feature devices which are formed by cutting elaborate kirigami patterns which provide compressible regions, regions with finger spikes, and regions which are asymmetric so as to allow for formation of an angled branch.

Figure 12:
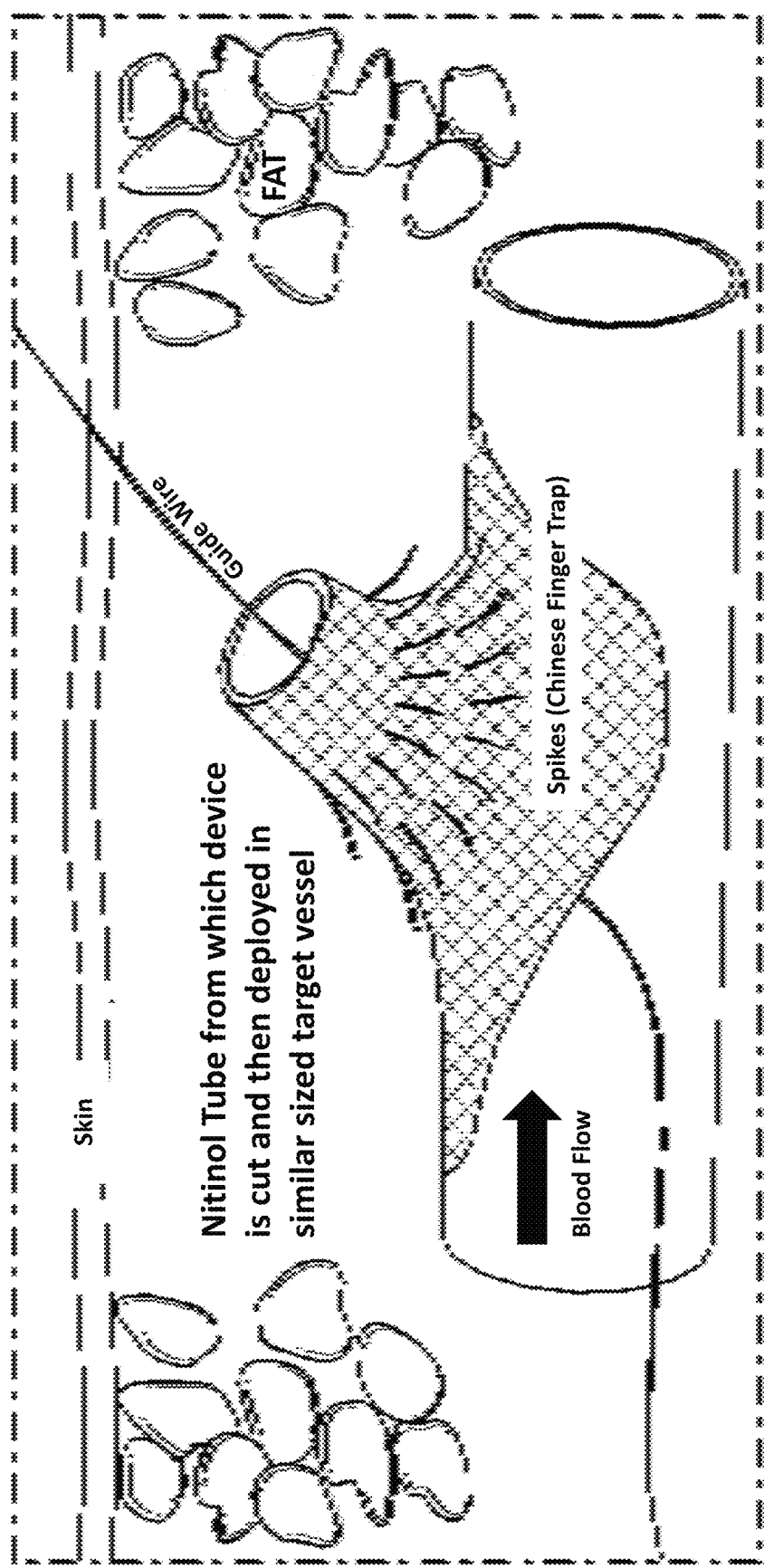
FIG. 12 shows a schematic drawing of a device of the present invention having been cut out of a Nitinol tube to create an expandable element and having been placed in a blood vessel to form an anastomosis.

Referring now to FIG. 12, the present invention may feature devices which are cut from a nitinol tube before being inserted underneath skin and fat to allow for blood flow through a branched anastomosis. The devices may feature spikes which allow the device to seal against the vessel wall in the manner of a Chinese finger trap. That's is, the seal may become stronger with more force applied to break the seal.

Figure 13:
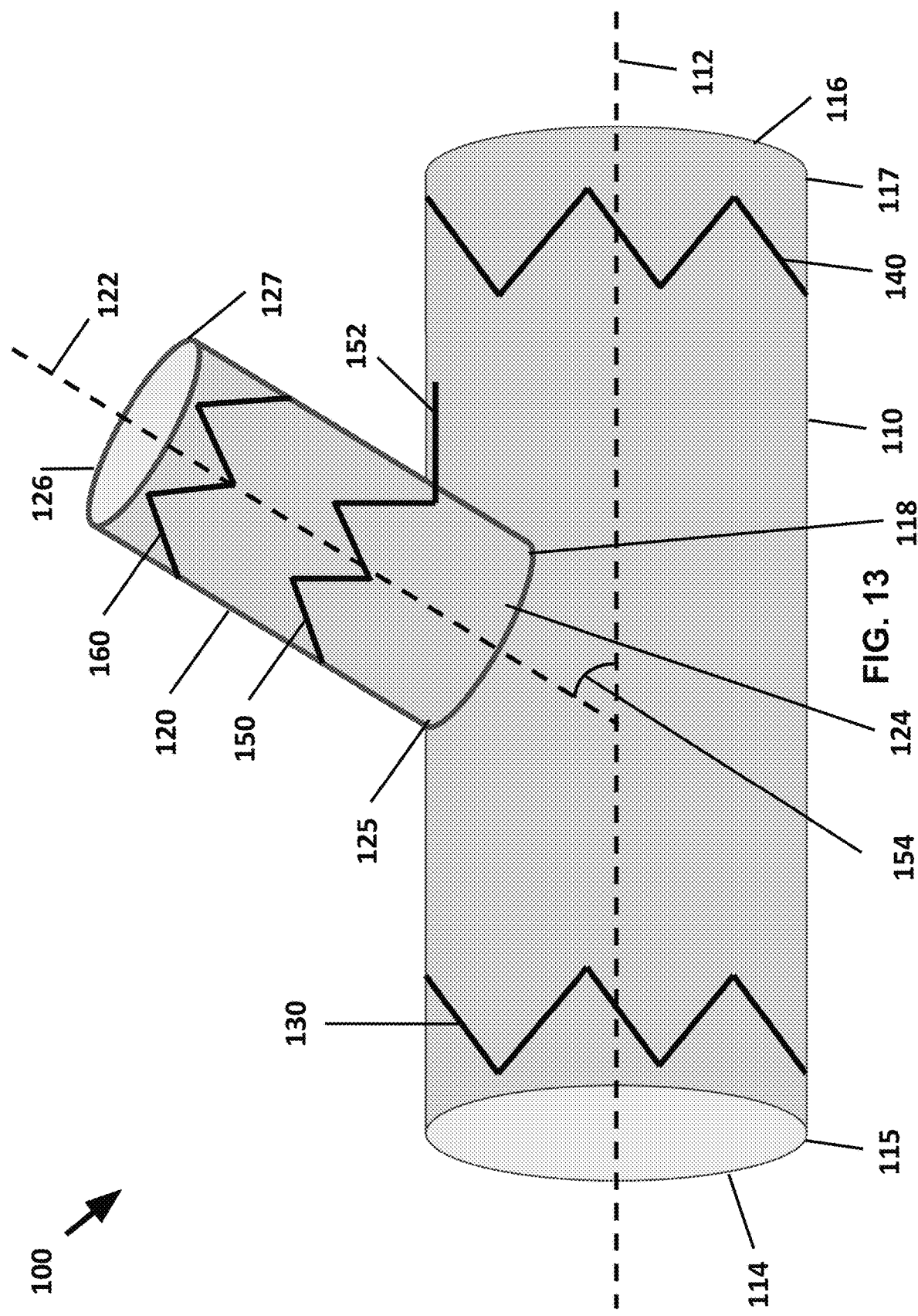
FIG. 13 shows a schematic drawing of an anastomosis device of the present invention having four collapsible rings.

Referring now to FIG. 13, the present invention features a branched anastomosis device (100). In a preferred embodiment, the device may comprise a main channel (110) having an axis A (112), a proximal opening (114) at a proximal end (115), a distal opening (116) at a distal end (117), and a side opening (118) between the proximal and the distal ends, and a branch channel (120) having an axis B (122), a proximal opening (124) at a proximal end (125), and a distal opening (126) at a distal end (127), the proximal opening (124) fluidly connected to the side opening (118) of the main channel (110). In another embodiment, the device (100) may comprise a first collapsible ring (130), the ring coaxially disposed along axis A (112), inside the proximal opening (114) of the main channel (110); a second collapsible ring (140), the ring coaxially disposed along axis A (112), inside the distal opening (116) of the main channel (110); and a third collapsible ring (150), the ring coaxially disposed along axis B (122), inside the proximal opening (124) of the branch channel (120). In some embodiments, the device (100) may comprise a fourth collapsible ring (160), the ring coaxially disposed along axis B (122), inside the distal opening (126) of the branch channel (120). In some other embodiments, axis A and axis B may intersect to form an angle (154).

According to one embodiment, the collapsible rings may comprise a metal, a nitinol material, a stainless steel material, or a titanium material. In another embodiment, the collapsible rings may comprise a zigzag shape. In still another embodiment, the collapsible rings can collapse towards their respective axes, and the two axes can collapse towards each other to yield a collapsed position of the device (100) with a collapsed diameter which is less than about 10% of an expanded diameter. In other embodiments, the collapsed diameter may be less than about 1-2, 2-3, 3-4, 4-5, 5-6, 6-7, 7-8, 8-9, 9-10, 15-20, 20-25, 25-30, 30-40, or 40-50% of the expanded diameter. In still other embodiments, the collapsed diameter may be less than about 1, 2, 3, 4, 5, 6, 7, 8, 9, 15, 20, 25, 30, 40 or 50 percent of the expanded diameter.

Figure 14A:
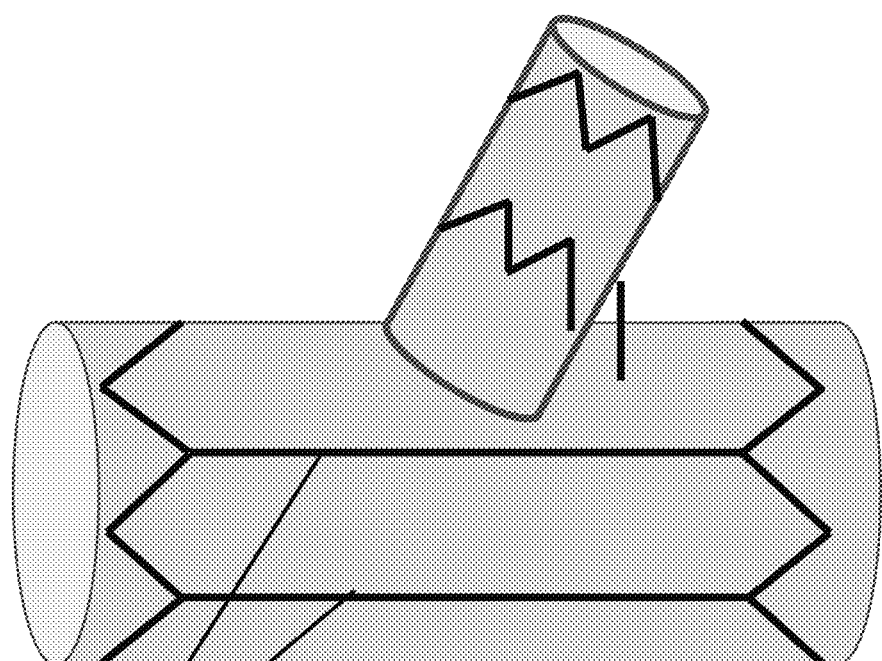
FIG. 14A shows a schematic drawing of an anastomosis device of the present invention having struts connecting the first and second collapsible rings.
Figure 14B:
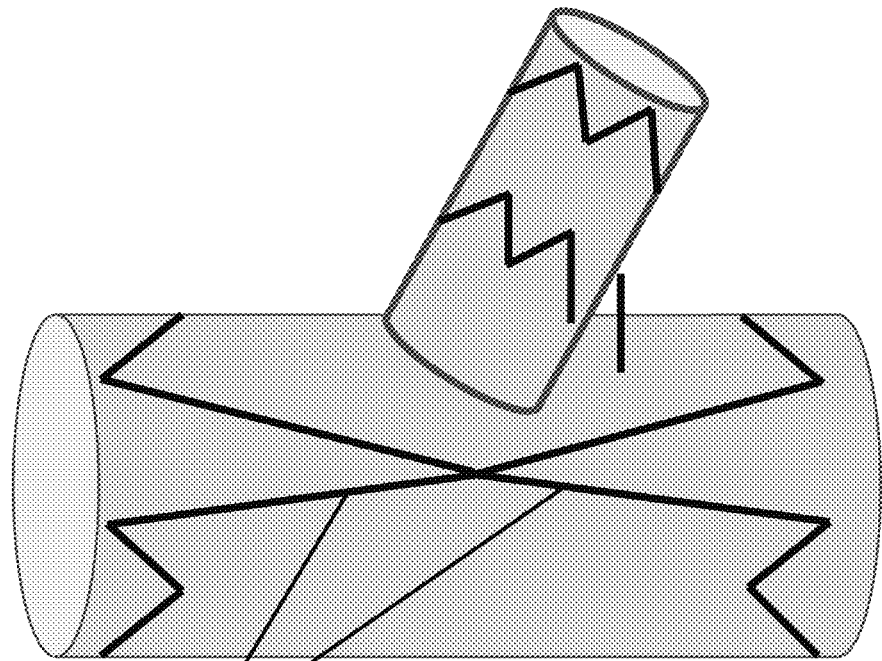
FIG. 14B shows a schematic drawing of an anastomosis device of the present invention having struts connecting the first and second collapsible rings.

Referring now to FIG. 14A and FIG. 14B, the devices of the present invention may feature one or more struts (190) connecting the first collapsible ring (130) and the second collapsible ring (140). In some embodiments, the struts may hold the two rings at a fixed distance. In one embodiment, the struts may be straight struts between vertices of the two rings. In another embodiment, the struts may be formed by elongated vertices of the two rings which are connected with each other. As a non-limiting example, the device may comprise 1, 2, 3, 4, 5, 6, 7, 8, 9, 10, 11, 12, or more struts. Without wishing to limit the present invention to any particular theory or mechanism, it is believed that these struts (190) may allow for the device to be pulled back within the vessel after it is inserted along the guidewire such that the first collapsible ring (130) and the second collapsible ring (140) are positioned on either side of the incision into the vessel. Without the struts (190), it may be difficult to push the one of the rings within the vessel in the opposite direction as from the guidewire.

Figure 15A:
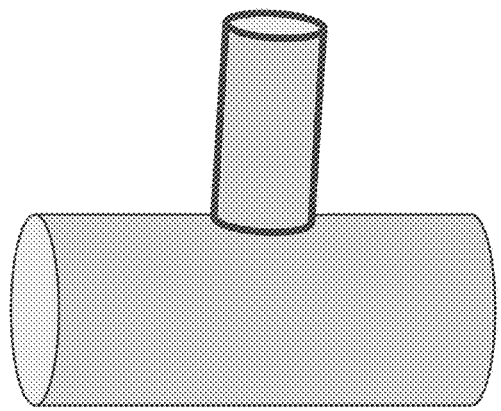
FIG. 15A shows a side view schematic drawing of an anastomosis device of the present invention having a wide angle between the main channel and the branch channel.
Figure 15B:
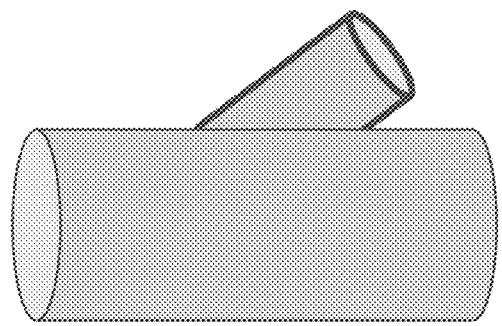
FIG. 15B shows a side view schematic drawing of an anastomosis device of the present invention having a narrow angle between the main channel and the branch channel.

In a selected embodiment, the third collapsible ring (150) may comprise an angled barb (152) which interfaces with the main channel (110) and aligns with axis A (112) to set an angle (154) between the main channel and the branch channel. In one selected embodiment, the angle Θ(154) may be about 25-35 degrees. In another selected embodiment, the angle (154) may be about 1-5, 2-7, 5-10, 10-15 15-20, 20-25, 25-30, 35-40, 40-45, 45-50, 50-55, 55-60, 60-65-70, 70-75, 75-80, 80-85, or 85-90 degrees. In one selected embodiment, the angle Θ(154) may be about 30 degrees. In another selected embodiment, the angle (154) may be about 1, 2, 5, 10, 15, 20, 25, 35, 40, 45, 50, 55, 60, 65, 70, 75, 80, 85, or 90 degrees. Devices with wide and narrow angles between the main channel and the branch channel are shown in FIG. and FIG. 15B.

Figure 15C:
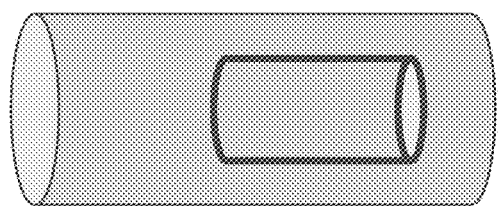
FIG. 15C shows a top view schematic drawing of an anastomosis device of the present invention having the branch channel aligned with the main channel.
Figure 15D:
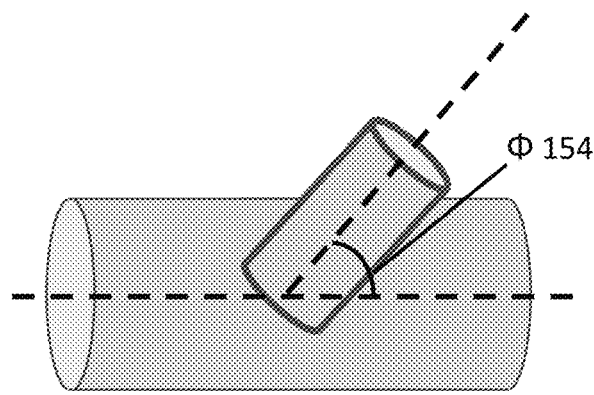
FIG. 15D shows a top view schematic drawing of an anastomosis device of the present invention having the branch channel at an angle from the main channel.

Referring now to FIG. 15C and FIG. 15D, the devices of the present invention may have a second angle Φ between the main channel and the branch channel. This second angle is defined by the angle between the branch channel and the plane which bisects both ends of the main channel and the side opening of the main channel. When this second angle is 0, the branch channel and the main channel are aligned and when it is 90 degrees, the branch channel and the main channel are perpendicular.

According to some embodiments, the the device (100) may be configured to fit inside a blood vessel, with the branch channel (120) protruding from an incision in the blood vessel to form a vascular anastomosis. As shown in FIG. 9B, the branch channel (120) may comprise radial spikes (128) to hold the proximal end (125) of the branch channel (120) against the blood vessel. In some preferred embodiments, the third collapsible ring (150) may fit in a space between the first collapsible ring (130) and the second collapsible ring (140) when the device (100) is collapsed.

According to one embodiment, the device (100) may comprise a flexible material which is coated over the collapsible rings to form the main channel (110) and the branch channel (120). As non-limiting examples, the flexible material may be a plastic material, a fabric material, a Dacron material, a poly-tetrafluoroethylene (PTFE) material, or an expanded poly-tetrafluoroethylene material (EPTFE). Without wishing to limit the invention to any particular theory or mechanism, this flexibility may allow the device (100) to be collapsed and fit within a delivery sheath (180). In further embodiments, the device (100) may be passed over a wire (170) and inserted into a blood vessel.

In still further embodiments, the first and second collapsible rings may have an expanded diameter which is about 15-20% greater than the diameter of the blood vessel. In alternative embodiments, the first and second collapsible rings may have an expanded diameter which is about 1, 2, 5, 10, 15, 20, 25, 30, 35, 40, 45, or 50 percent greater than the diameter of the blood vessel. In other alternative embodiments, the first and second collapsible rings may have an expanded diameter which is about 1-2, 2-5, 5-10, 10-15, 15-25, 25-30, 30-35, 35-40, 40-45, or percent greater than the diameter of the blood vessel. In some embodiments, the diameter of the blood vessel may be between about 2 and 10 mm. In other embodiments, the diameter of the blood vessel may be between about 1 and 10, 3 and 10, 4 and 10, 5 and 10, 6 and 10, 7 and 10, 8 and 10, 9 and 10, 1 and 20, 3 and 20, 4 and 20, 5 and 20, 6 and 20, 7 and 8 and 20, 9 and 20, or 20 and 30 mm.

Figure 16A:
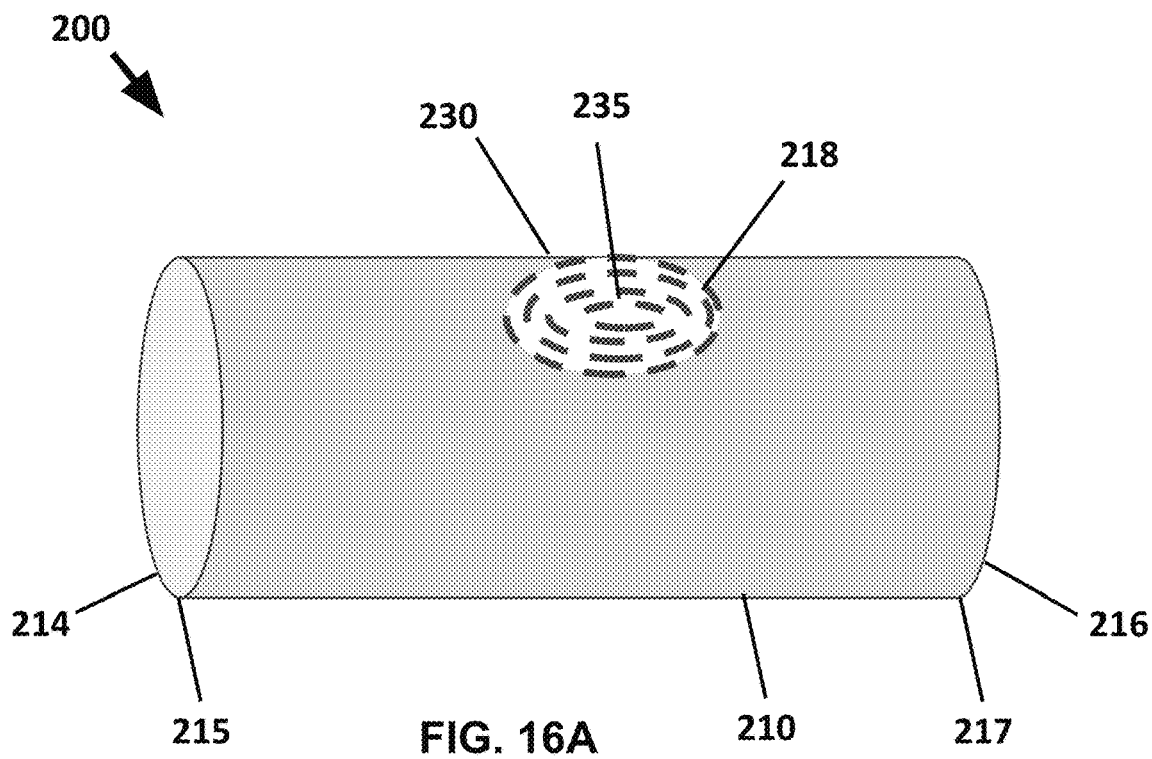
FIG. 16A shows a schematic drawing of a tubular device of the present invention having a pattern cut in the side of the tube to create an expandable element which can be pulled from the surface of the parent tubular material to make a three-dimensional branch shape.
Figure 16B:
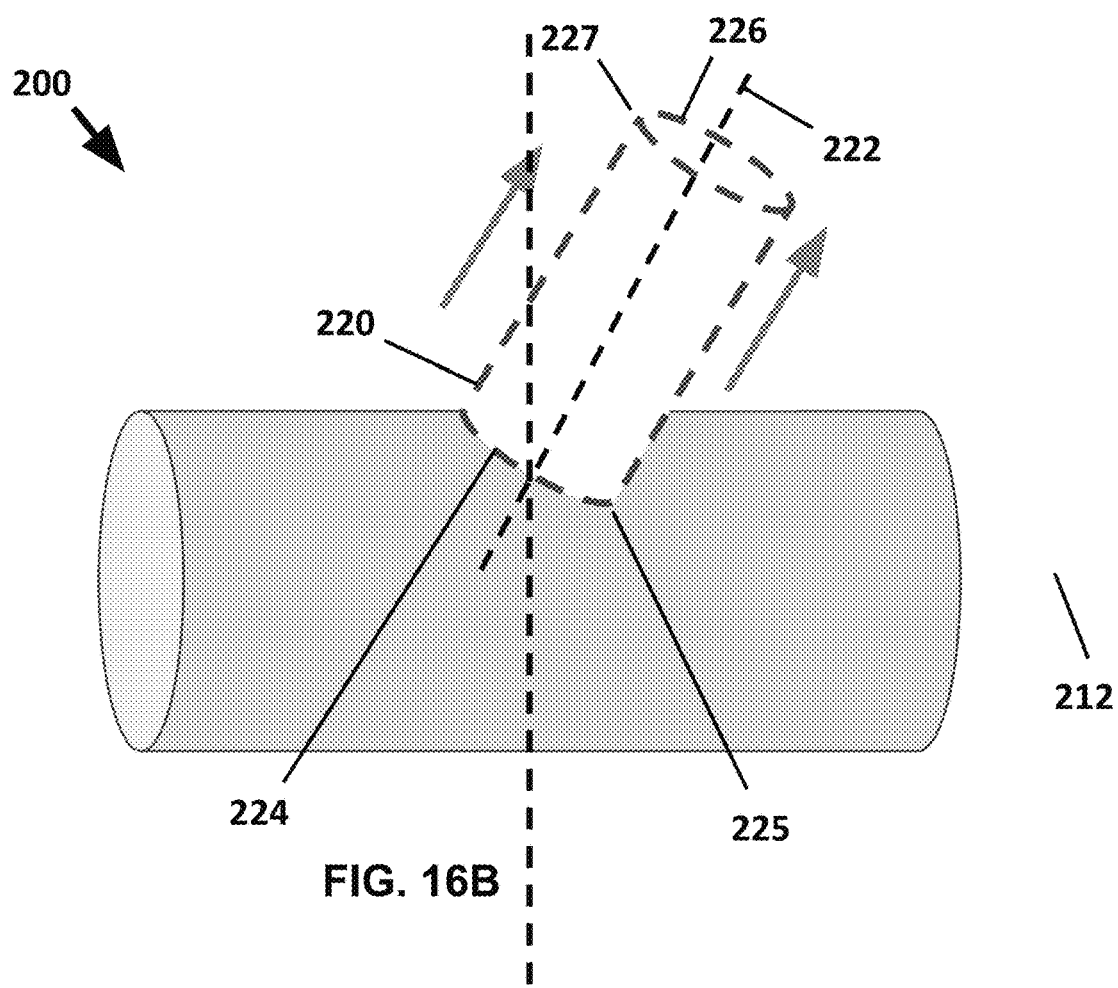
FIG. 16B shows a schematic drawing of the device shown in FIG. 13A, having had the patterned portion of the tube pulled away from the center of the tube to form a three-dimensional branch shape.

Referring now to FIG. 16A and FIG. 16B, the present invention features a branched anastomosis device (200) comprising: a main channel (210) having an axis A (212), a proximal opening (214) at a proximal end (215), a distal opening (216) at a distal end (217), and a side opening (218) between the proximal and distal ends; and a pattern (230) cut disposed around the side opening (218), having a central portion (235) such that pulling the central portion (235) along an axis B (222) forms an expandable branch channel (220) along axis B (222), having a proximal opening (224) at a proximal end (225), and a distal opening (226) at a distal end (227), the proximal opening (224) fluidly connected to the side opening (218) of the main channel (210). In preferred embodiments, the expandable branch channel (220) is configured to form an anastomosis.

According to some embodiments, the pattern (230) may be a kirigami pattern. In further embodiments, the pattern may be cut in a nitinol material. In still further embodiments, the expandable branch channel may be coated with a flexible material. As a non-limiting example, the flexible material may be a poly-tetrafluoroethylene material. In one embodiment, an angle between the main channel and the expandable branch channel may be about 25-35 degrees. In another embodiment, the angle may be about 1-5, 2-7, 5-10, 10-15 15-20, 20-25, 25-30, 35-40, 45-50, 50-55, 55-60, 60-65, 65-70, 70-75, 75-80, 80-85, or 85-90 degrees. In one embodiment, an angle between the main channel and the expandable branch channel may be about 30 degrees. In another embodiment, the angle between the main channel and the expandable branch channel may be about 1, 2, 5, 10, 15, 20, 25, 35, 40, 45, 50, 55, 60 65, 70, 80, 85, or 90 degrees.

In some preferred embodiments, the device (200) may be configured to fit inside a blood vessel, with the expandable branch channel protruding from an incision in the blood vessel. In other preferred embodiments, the device (200) may collapse to fit within a delivery sheath (280). In still other preferred embodiments, the device (200) may be passed over a wire (270) and inserted into a blood vessel.

The present invention also features methods of forming a vascular anastomosis. As a non-limiting example, the method may comprise: inserting a wire (170) into a blood vessel at a position for an anastomosis; passing a cutting device (174) over the wire (170) to make an incision in the blood vessel; providing a collapsed anastomosis device (100) inside of a delivery sheath (180); passing the collapsed device (100) and delivery sheath (180) over the wire (170) and through the incision into the blood vessel; withdrawing the delivery sheath (180) to expand the collapsed device (100); and positioning the expanded device (100) within the blood vessel such that a branch channel (120) of the device (100) extends out of the incision to form the anastomosis.

As another non-limiting example, the method of forming a vascular anastomosis may comprise: inserting a wire (270) into a blood vessel at a position for an anastomosis; passing a cutting device (274) over the wire (270) to make an incision in the blood vessel; providing a collapsed anastomosis device (200) inside of a delivery sheath (280); passing the collapsed device (200) and delivery sheath (280) over the wire (270) and through the incision into the blood vessel; withdrawing the delivery sheath (280) to expand the collapsed device (200); positioning the expanded device (200) within the blood vessel such that a pattern (230) cut into a side of the device (200) is aligned with the incision; and pulling a central portion (235) of a pattern (230) to form an expandable branch channel (220) which extends out of the incision to form the anastomosis. In some embodiments, a a second wire may be used to position the device. In other embodiments, a branched balloon may be used to expand the collapsed device. In still other embodiments, the device may comprise a plurality of collapsible rings.

As used herein, the term "about" refers to plus or minus 10% of the referenced number. Various modifications of the invention, in addition to those described herein, will be apparent to those skilled in the art from the foregoing description.

Such modifications are also intended to fall within the scope of the appended claims. Each reference cited in the present application is incorporated herein by reference in its entirety. Although there has been shown and described the preferred embodiment of the present invention, it will be readily apparent to those skilled in the art that modifications may be made thereto which do not exceed the scope of the appended claims. Therefore, the scope of the invention is only to be limited by the following claims.

Reference numbers recited in the claims are exemplary and for ease of review by the patent office only, and are not limiting in any way. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting of", and as such the written description requirement for claiming one or more embodiments of the present invention using the phrase "consisting of" is met.

What is claimed is:

1. A branched anastomosis device (100), configured for minimally invasive implantation, the device (100) comprising:
   a. a main channel (110) having an axis A (112), a proximal opening (114) at a proximal end (115), a distal opening (116) at a distal end (117), and a side opening (118) between the proximal and the distal ends;
   b. a branch channel (120) having an axis B (122), a proximal opening (124) at a proximal end (125), and a distal opening (126) at a distal end (127), the proximal opening (124) of the branch channel (120) fluidly connected to the side opening (118) of the main channel (110);
   c. a first collapsible ring (130), the first collapsible ring (130) coaxially disposed along axis A (112), inside the proximal opening (114) of the main channel (110);
   d. a second collapsible ring (140), the second collapsible ring (140) coaxially disposed along axis A (112), inside the distal opening (116) of the main channel (110); and
   e. a third collapsible ring (150), the third collapsible ring (150) coaxially disposed along axis B (122), inside the proximal opening (124) of the branch channel (120), wherein the third collapsible ring (150) comprises an angled barb (152) which interfaces with the main channel (110) and aligns with axis A (112) to set the angle (154) between the main channel (110) and the branch channel (120);
   wherein axis A and axis B intersect to form an angle (154).

2. The branched anastomosis device (100) of claim 1, wherein the device (100) comprises a flexible material which is coated over the first, second, and third collapsible rings to form the main channel (110) and the branch channel (120).

3. The branched anastomosis device (100) of claim 1, wherein the device (100) additionally comprises a fourth collapsible ring (160), the fourth collapsible ring (160) coaxially disposed along axis B (122), inside the distal opening (126) of the branch channel (120).

4. The branched anastomosis device (100) of claim 1, wherein the first, second, and third collapsible rings are configured to collapse towards their respective axes, and the two axes are configured to collapse towards each other to yield a collapsed position of the device (100) with a collapsed diameter which is less than about 10% of an expanded diameter of the device (100).

5. The branched anastomosis device (100) of claim 1, wherein the third collapsible ring (150) is configured to fit in a space between the first collapsible ring (130) and the second collapsible ring (140) when the device (100) is collapsed.

6. The branched anastomosis device (100) of claim 1, wherein the device (100) is configured to fit inside a blood vessel, with the branch channel (120) protruding from an incision in the blood vessel to form a vascular anastomosis.

7. The branched anastomosis device (100) of claim 1, wherein the branch channel (120) comprises radial spikes (128) to hold the proximal end (125) of the branch channel (120) against a blood vessel.

8. The branched anastomosis device (100) of claim 7, wherein the first and second collapsible rings are adapted to be deployed in the blood vessel with an expanded diameter of the first and second collapsible rings to be about 15-20% greater than the diameter of the blood vessel.

9. The branched anastomosis device (100) of claim 1, wherein the device (100) comprises one or more struts (190) connecting the first collapsible ring (130) and the second collapsible ring (140).

10. The branched anastomosis device (100) of claim 9, wherein the one or more struts (190) hold the first and second collapsible rings at a fixed distance from each other.

* * * * *